United States Patent
Johnson et al.

(10) Patent No.: US 10,835,415 B2
(45) Date of Patent: Nov. 17, 2020

(54) THERAPEUTIC EYE POD SYSTEM

(71) Applicants: Robert W. Johnson, Pearl River, LA (US); Kathy L. Johnson, Pearl River, LA (US); Charles W. Lanusse, Opelousas, LA (US)

(72) Inventors: Robert W. Johnson, Pearl River, LA (US); Kathy L. Johnson, Pearl River, LA (US); Charles W. Lanusse, Opelousas, LA (US)

( * ) Notice: Subject to any disclaimer, the term of this patent is extended or adjusted under 35 U.S.C. 154(b) by 0 days.

(21) Appl. No.: 16/009,299

(22) Filed: Jun. 15, 2018

(65) Prior Publication Data
US 2018/0289533 A1    Oct. 11, 2018

Related U.S. Application Data

(63) Continuation-in-part of application No. 15/423,184, filed on Feb. 2, 2017, now Pat. No. 9,999,539.

(51) Int. Cl.
| | | |
|---|---|---|
| *A61F 7/00* | (2006.01) | |
| *A61F 7/02* | (2006.01) | |
| *A61B 50/31* | (2016.01) | |

(52) U.S. Cl.
CPC ............ *A61F 7/0241* (2013.01); *A61B 50/31* (2016.02); *A61F 7/02* (2013.01); *A61F 2007/0004* (2013.01); *A61F 2007/0076* (2013.01); *A61F 2007/0078* (2013.01); *A61F 2007/0225* (2013.01); *A61F 2007/0295* (2013.01)

(58) Field of Classification Search
CPC .. F25B 21/02; F25B 21/04; F25B 2321/0212; F25B 2321/0251; F25B 2321/023; H05B 1/00
See application file for complete search history.

(56) References Cited

U.S. PATENT DOCUMENTS

| | | | |
|---|---|---|---|
| 3,768,485 A | 10/1973 | Linick | |
| 5,301,508 A * | 4/1994 | Kahl | F25B 21/02 62/3.62 |
| 5,319,937 A * | 6/1994 | Fritsch | F25B 21/04 292/DIG. 38 |
| 6,658,857 B1 * | 12/2003 | George | F25B 21/04 165/121 |
| 8,784,391 B1 | 7/2014 | Biser | |
| 10,132,533 B2 * | 11/2018 | Oh | B60N 3/104 |
| 2008/0296286 A1 * | 12/2008 | Liang | A61F 7/02 219/528 |
| 2009/0287283 A1 | 11/2009 | Biser | |
| 2009/0288800 A1 * | 11/2009 | Kang | B60N 2/793 165/42 |
| 2015/0159924 A1 * | 6/2015 | Calderon | F25D 11/006 62/3.6 |
| 2016/0236605 A1 * | 8/2016 | Doi | B60N 3/104 |
| 2017/0049614 A1 | 2/2017 | Paulson | |

* cited by examiner

*Primary Examiner* — Michael F Peffley
(74) *Attorney, Agent, or Firm* — James Creighton Wray

(57) ABSTRACT

An orbital temperature treatment kit has a new container base, hinged cover and handle. An inner partition in the base is a mount for electrical features and a heat exchanger with transfer fins and a heat sink. The inner partition has recesses for temperature change of pods held in spaces between parallel fins. The frame for holding the pods in place for treatment has two large lenses, a nose piece joining the lenses and hinged temples. The lenses support slotted receivers with fasteners that engage fasteners on tabs attached to the pods.

19 Claims, 10 Drawing Sheets

THERAPEUTIC EYE POD SYSTEM

This application is a continuation-in-part of application Ser. No. 15/423,184 filed Feb. 2, 2017 which claims the benefit of U.S. Provisional Application No. 62/290,530 filed Feb. 3, 2016, which are hereby incorporated by reference in their entirety as if fully set forth herein.

BACKGROUND OF THE INVENTION

Needs exist for readily available and conveniently usable therapeutic temperature treatments.

SUMMARY OF THE INVENTION

The invention provides method and apparatus for orbital heating or cooling pods. New pod attachments and holders are provided for applying temperature treatment to bodies of users and particularly to orbital areas of faces. New frames support the heating or cooling pods against the orbital areas. The pods have at least one tab connected to and extending from each of the pods. A fastener is provided on an end of the tab remote from the pod.

For use on orbital areas, the frame has an attachment for contacting a head of a user and for receiving and holding the tab and holding the pod against the orbital area. The frame has a cross member having one or more cross pieces. A nose piece connects to a center of the cross member. Hinges are provided at opposite ends of the cross member. Temples are connected to the hinges. One or more receivers on the cross member receive and hold the tab. The one or more receivers in one form are one or more complementary fasteners for connecting to the fastener on a tab of a pod. The fasteners and the one or more complementary fasteners are cooperating multiple miniature magnetic and metal fasteners in one embodiment. A downward extension from the frame holds the pod rearward into the orbital area.

In one embodiment, the one or more cross pieces are first and second lenses. A nose piece connects the first and second lenses. The hinges are connected to the first and second lenses remote from the nose piece. The receivers are connected to tops of the first and second lenses. In one form, the receivers are upward extensions that have downward opening grooves holding them on tops of the lenses. The receivers have complementary fasteners for connecting to the fasteners on the tabs that are connected to the one or more pods. The complementary fasteners on the receivers are directed outward so that the tabs have to be looped over the tops of the receivers.

The entire apparatus includes a pod storer and temperature changer for holding and changing temperature of the one or more pods. The storer and temperature changer are in a container with an inner partition. A lower surface of the partition covers electrical connections and controls. A temperature changer has temperature changing fins, plate, a heat sink and a fan for passing air across the heat sink. In one form the temperature changer is a Peltier cooling apparatus.

A deep container base is provided with an inner partition. The inner partition has an upper surface with first paired cavities for holding pods adjacent the temperature changer fins. The inner partition has a second cavity for additional holding pods, a third cavity for holding the frame and a fourth cavity for holding electrical connectors.

The temperature changer and electrical connections, controls, transformers and converters are mounted on the lower side of the inner partition.

A handle is connected to the container base. At least one hinge is connected to the container, and a cover is connected to the at least one hinge.

The new orbital area temperature treatment combination has a container, an inner partition in the container, a temperature changer having heat exchange fins and a heat sink, and electrical connections and controls in the container mounted below the inner partition. Recesses in a top of the inner partition include a first pair of recesses positioned near the heat exchange fins. The paired recessed are adapted for holding at least one orbital area temperature treatment pod near the heat exchange fins. Additional recesses include a recess for holding additional pods, a recess for holding an electrical connector and remote control and a recess for holding a frame. The frame is configured for attaching one or more temperature treatment pods, and positioning the temperature treatment pods against an orbital area of a user's head.

In one form, the electrical connections and controls and the heat exchanger are mounted on a bottom surface of the inner partition, and the recesses are in the top surface of the inner partition. The container base has apertures for circulating ambient air around the heat sink. Three parallel heat exchange fins change the temperature in two parallel recesses, and each recess is positioned between two of the heat exchange fins. The container base further has a handle, one or more hinges and a cover connected to the hinges.

The temperature treatment pods, the elongated control and electrical connector and the frame are included in the recesses when the apparatus is sold for use.

A carton encloses the container and hinged cover, the inner partition, the electrical connection and control, the temperature changer, the pods, the electrical connector, the frame, the handle and the cover as a complete system ready for shipment and use as instructed by a professional.

The new orbital temperature treatment kit includes a carrying case, an inner partition component, a power supply main with cord, a power supply auxiliary plug, a Peltier TE module, a thermal switch, a custom TE exchanger extrusion, insulation for TE extrusion, a DPDT switch, LED indicators, a 12 VDC entrance jack, six pods, a frame in the form of goggles, insulation, neodymium magnets, a retail box, labels and an instruction sheet.

These and further and other objects and features of the invention are apparent in the disclosure, which includes the above and ongoing written specification, with the claims and the drawings.

DETAILED DESCRIPTION

Figure 1:
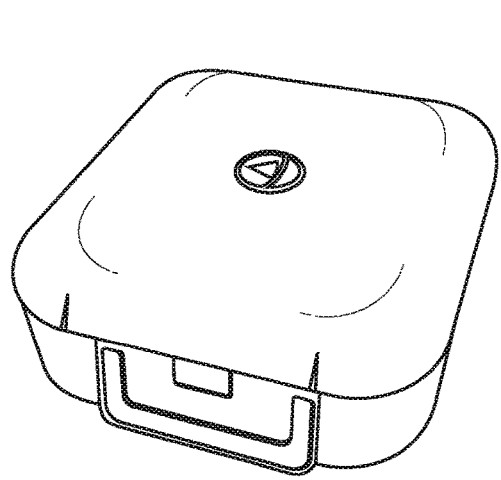
FIG. 1 is a view of the new container.

FIG. 1 is a view of the new kit container 100.

Figure 2:
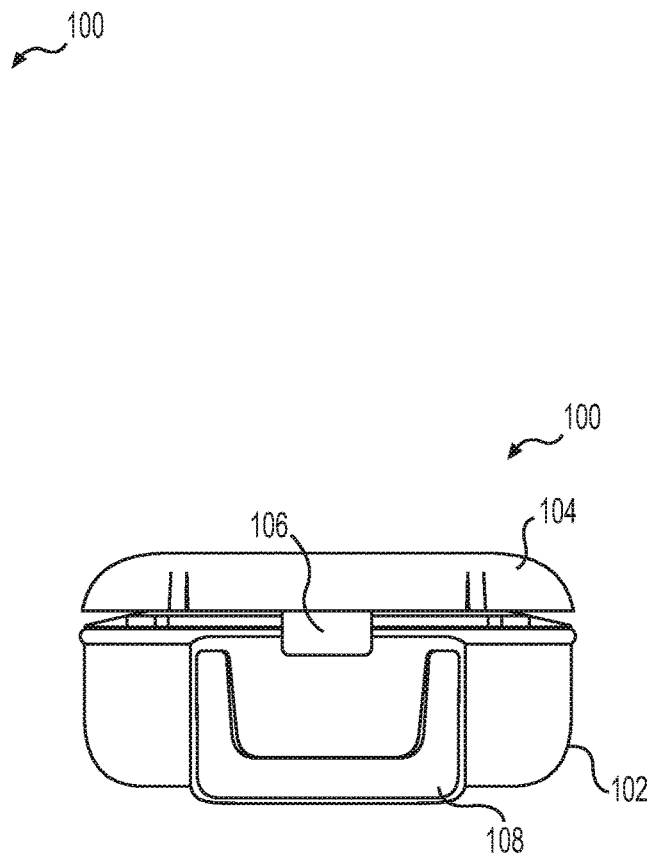
FIG. 2 is a view of the new container opening.

FIG. 2 is a view of the new kit container 100 opening showing the container base 102, the hinged cover 104, the latch 106 attached to the cover and the hinged handle 108 attached to the container base.

Figure 3:
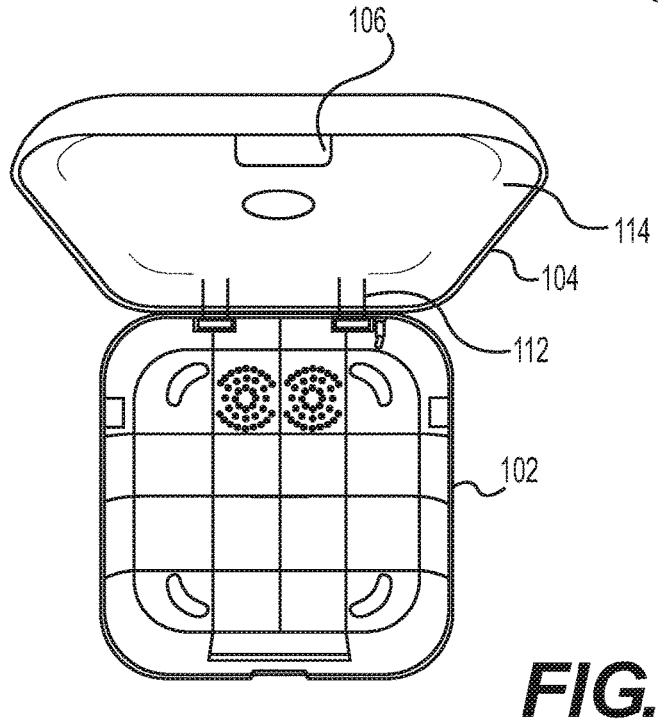
FIG. 3 is a view of the new container open without contents.

FIG. 3 is a view of the new container base 102 open without contents showing the cover 104 hinges 112, the instruction holder 114 in the cover and the cover latch 106.

Figure 4:
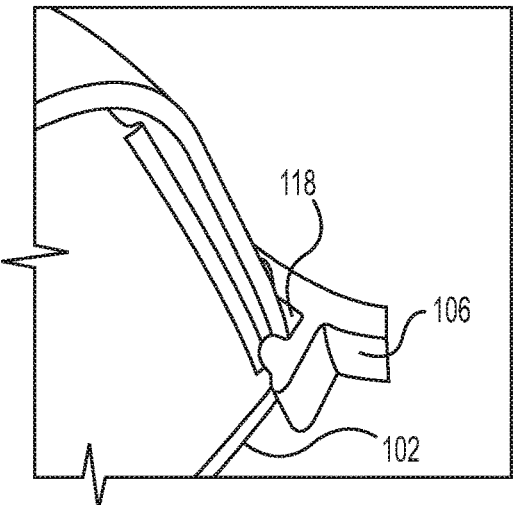
FIG. 4 is a view of the new container lock.

FIG. 4 is a detail of the container latch 106 cutaway to show the connection to the lip 118 extending from the container base 102.

Figure 5:
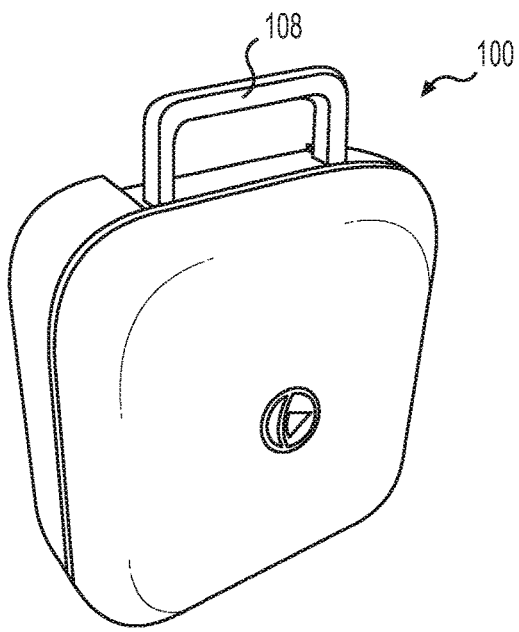
FIG. 5 is a view of the new container with the handle raised.

FIG. 5 is a view of the new kit container 100 with the handle 108 raised.

Figure 6:
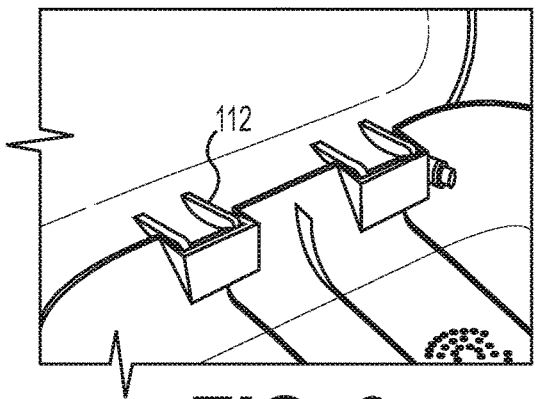
FIG. 6 is a view of the new container hinges.

FIG. 6 is a detail of the new kit container cover hinges 112.

Figure 7:
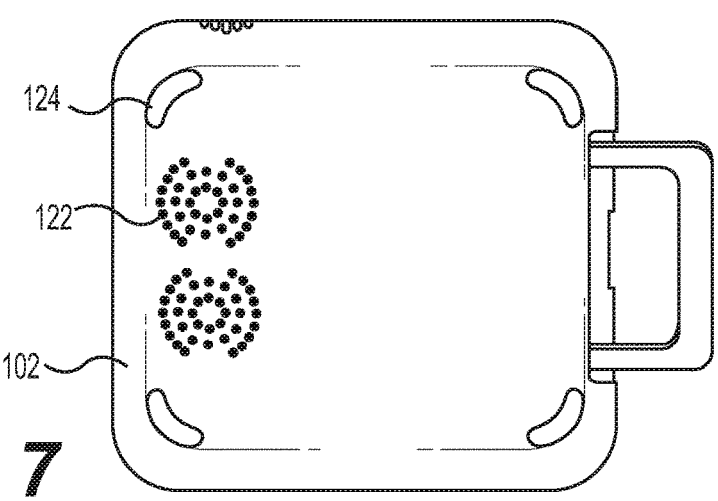
FIG. 7 is a bottom view of the new container.

FIG. 7 is a bottom view of the new kit container 100 showing the ambient air flow apertures 122 in the container base 102 for moving air through the heat sink. Curved lifts 124 in corners hold the container base 102 spaced above a surface on which it rests during use. Besides allowing free air movement, the curved corner lifts resist sliding on the underlying surface.

Figure 8:
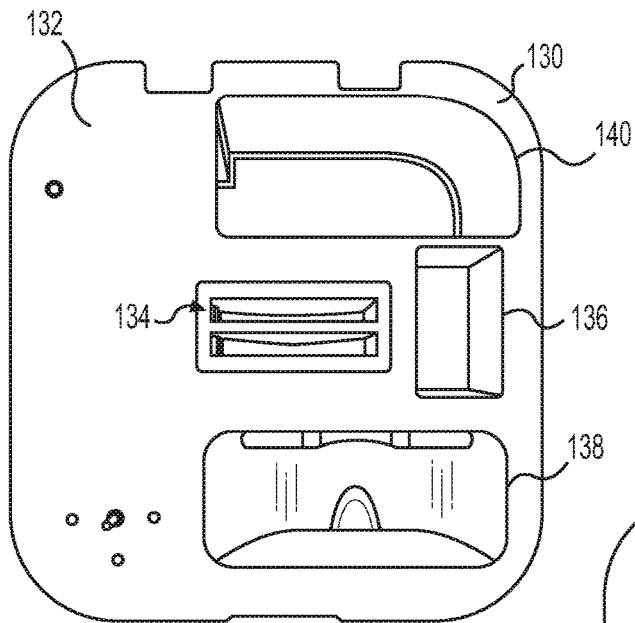
FIG. 8 is a top view of the partition for the new container.

FIG. 8 is a top view of the inner partition 130 for the new container base 102. The upper surface 132 of the inner partition has paired first recesses 134 for holding pods, the second recess 136 for holding additional pods, a third recess 138 for holding frame glasses and a fourth recess 140 for holding a remote control and an electrical connector.

Figure 9:
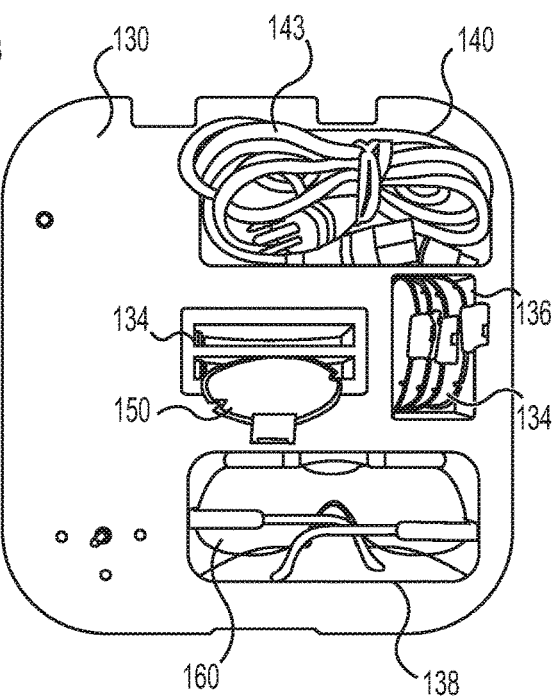
FIG. 9 is a top view of the partition for the new container with pods, frame and electrical connector in cavities.

FIG. 9 is a top view of the partition for the new container with pods 150, frame 160 and electrical connector 143 in recesses 134, 136, 138 and 140, respectively.

Figure 10:
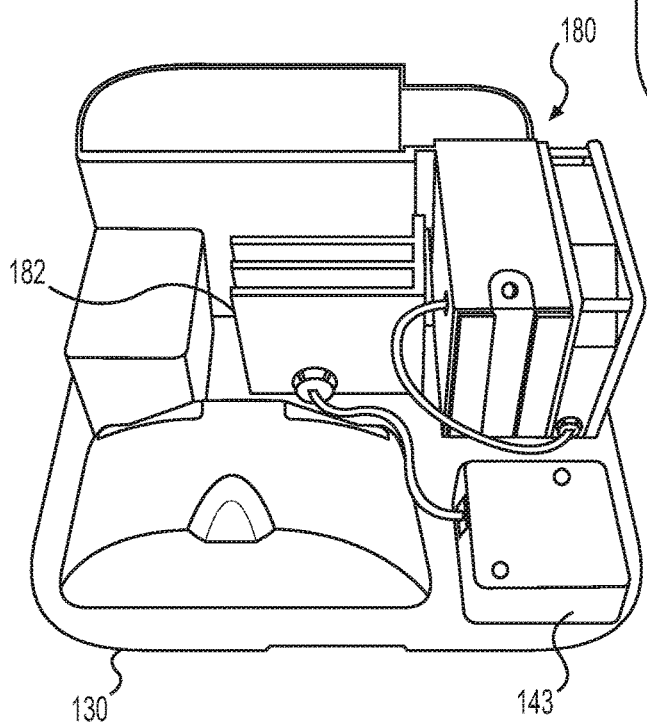
FIG. 10 is a bottom view of the new container with the electrical connections and control and the temperature changer mounted on the partition.

FIG. 10 is a bottom view of the inner partition 130 for new container base 102. Electrical connections and control 143 and the temperature changer 180 are mounted on the partition. Fins 182 extend from the temperature changer to transfer the new temperature to the pods 150 in the first paired recesses 134. Each of the paired recesses is positioned between two of the three fins 182.

Figure 11:
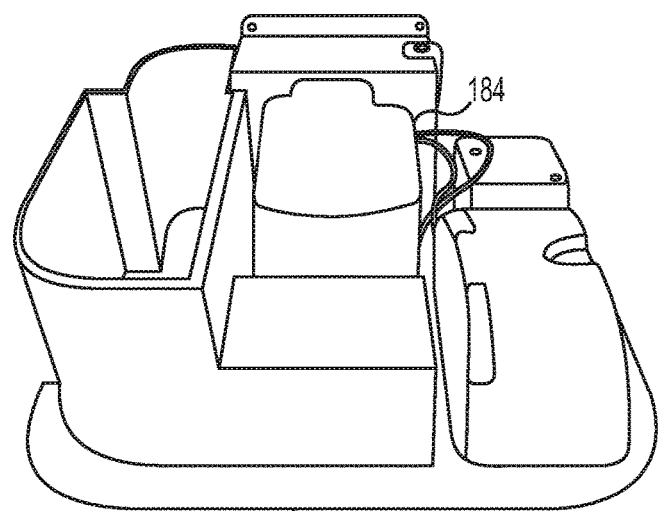
FIG. 11 is a left side view of the new container with the fins coverer.

FIG. 11 is a left side view of inner partition 130 for the new container kit base 102 with the fins 182 covered by an insulated cover 184 to concentrate the temperature change on the pods 150 within the first paired recesses 134.

Figure 12:
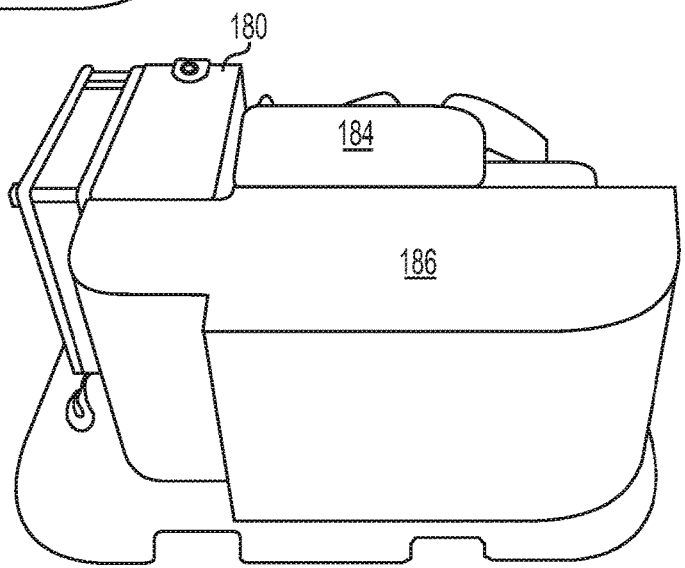
FIG. 12 is a bottom view of the new container with the left side of FIG. 11.

FIG. 12 is a bottom view of the inner partition 130 for the new container kit base 102 with the left side of FIG. 11. The container base is covered with insulated covers 184 and 186. The temperature changer 180 body remains exposed to air flow through apertures 122 in the container base 102, as shown in FIG. 7.

Figure 13:
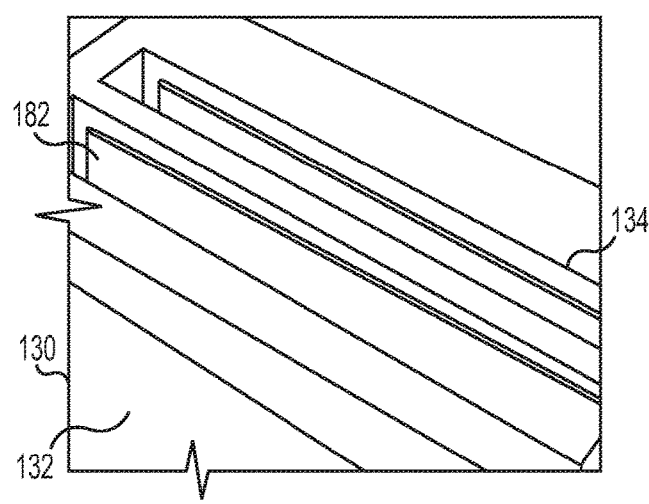
FIG. 13 is a detail of pod cavities for heat transfer.

FIG. 13 is a detail of paired pod recess openings 134 in the upper surface 132 of the inner partition 130 for exposure to the heat transfer fins 182.

Figure 14:
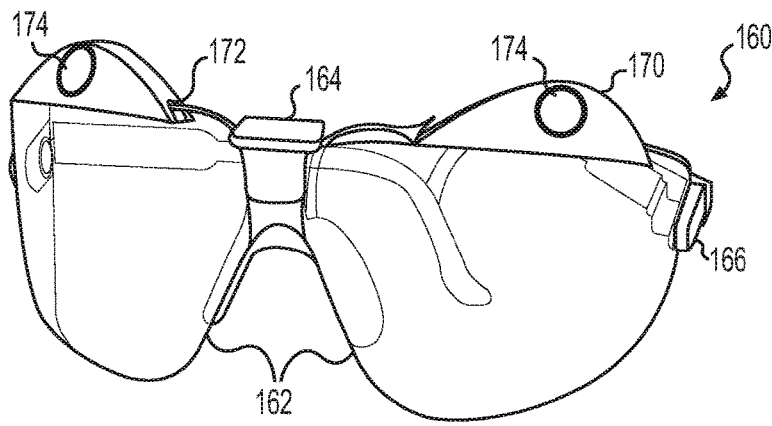
FIG. 14 is a front view of the frame.
Figure 15:
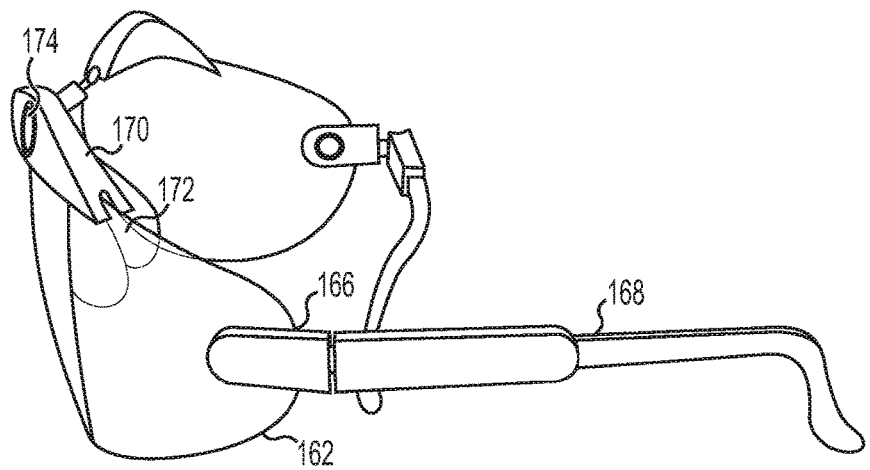
FIG. 15 is a side view of the frame.

FIG. 14 is a front view and FIG. 15 is a side view of one form of the frame 160 as shown in FIG. 9 within the third recess of the upper surface 132 of inner partition 130. The cross pieces of the cross member are lenses 162. Nose Piece 164 connects the lenses 162. Hinges 166 connect temples 168. Attachments 170 have grooves 172 which receive tops of the lenses 162. Fastener 174 cooperates with fasteners on connector tabs that extend from pods 150 to hold the tabs and pods in place.

Figure 16:
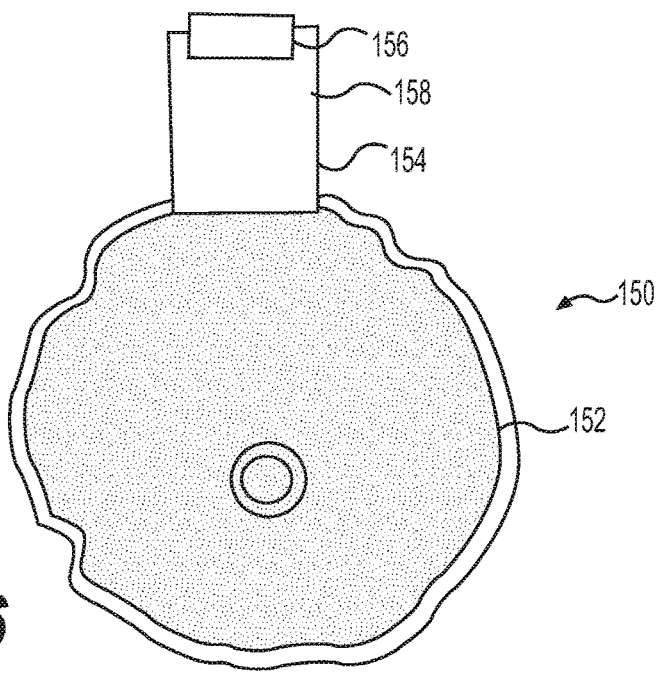
FIG. 16 is a front view of a pod.

FIG. 16 is a front view of a temperature treatment pod 150. A multiple layered curvilinear body 152 is filled with a temperature retaining liquid, gel or particles. A tab 154 extends from an edge of the body 152 of a pod 150. A fastener 156 is on the remote end 158 of the tab. Fastener 156 is a material that attracts magnetic lines of force, for example a metal or metal in a polymer.

Figure 17:
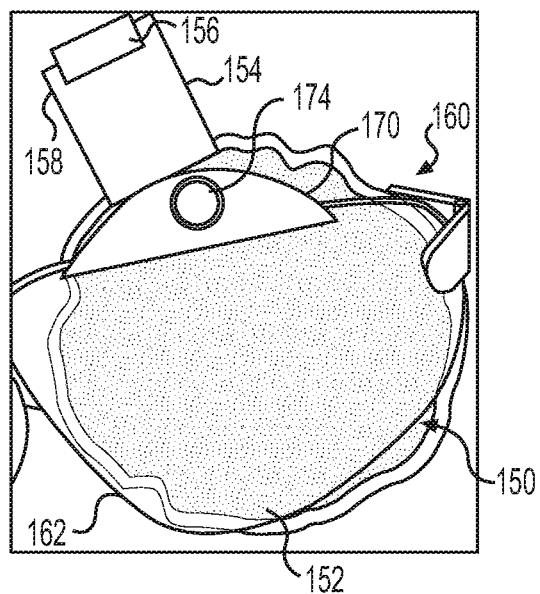
FIG. 17 shows the pod placed in the frame.
Figure 18:
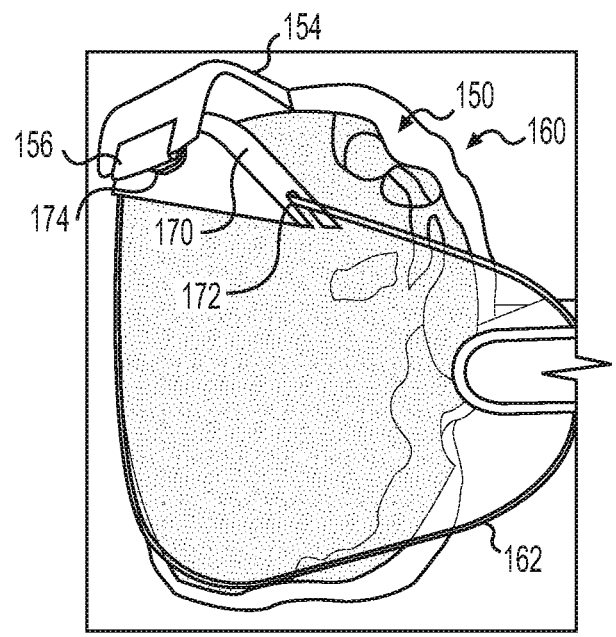
FIG. 18 shows connected fasteners of the pod and frame.

FIGS. 17 and 18 show the pod 150 placed in the frame 160. The tab 154 extends above one of the lenses 162 of frame 160. The tab 154 is folded over attachment 170, and the fastener 156 on the tab cooperates with the complementary fastener 174 on the frame attachment 170, holding the pod in place.

FIG. 18 shows connected fasteners 156 and 174 of the pod 150 and frame 160, respectively.

Figure 19:
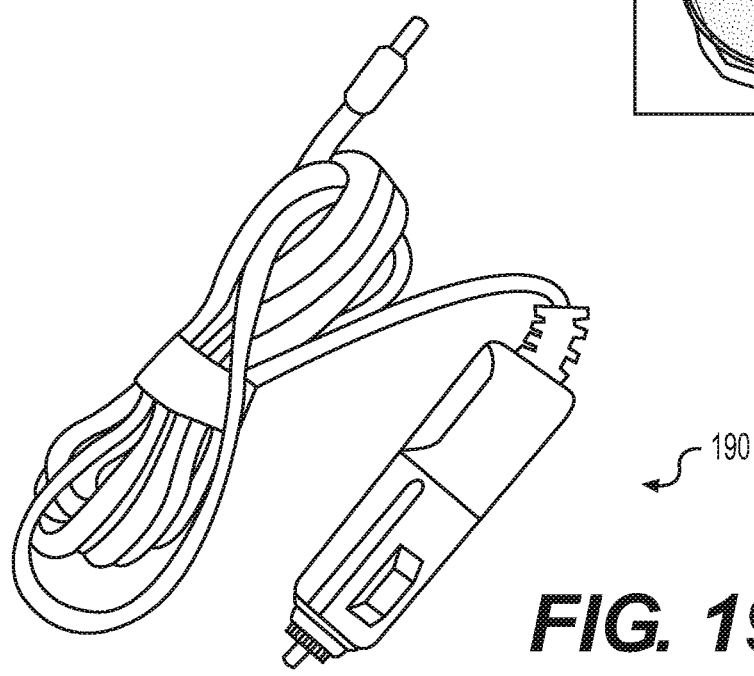
FIG. 19 shows an electrical control for the system.

FIG. 19 shows an electrical control connection 190 for connecting the system to a 12V 5 A source.

Figure 20:
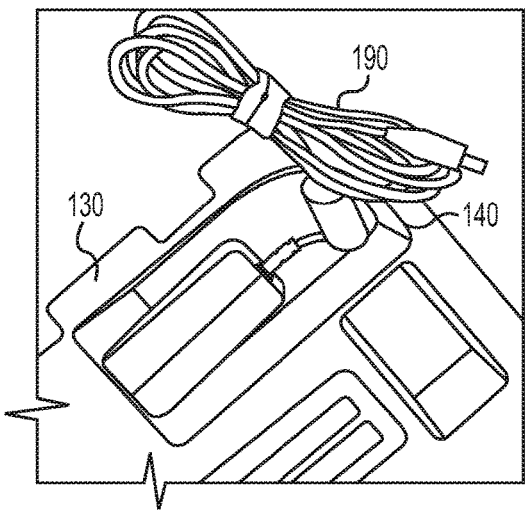
FIG. 20 shows the electrical control partially stored in a partition cavity.
Figure 21:
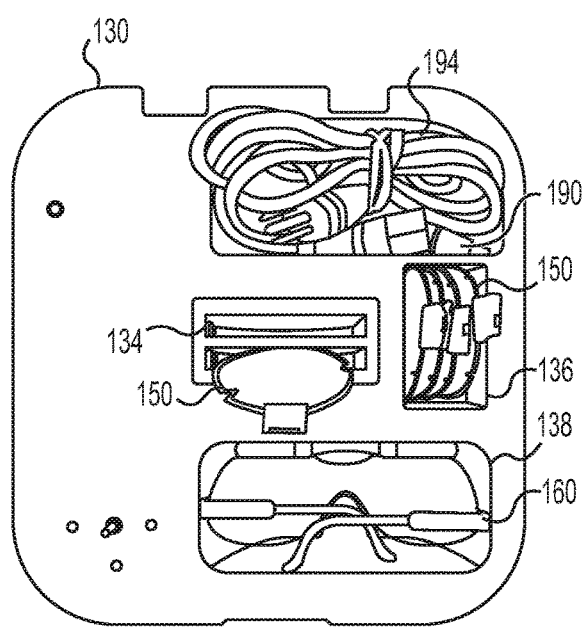
FIG. 21 shows the electrical control under the electrical connector stored in the partition cavity.

FIG. 20 shows the electrical control connection 190 partially stored in the fourth recess 140 of the inner partition 130. FIG. 21 shows the electrical control connection 190 under the electrical connector 194 stored in the fourth recess 140 of the inner partition 130. The pods 150 are held and cooled in the first paired recesses 134 and stored in the second recess 136. The frame 160 in the third recess 138.

Figure 22:
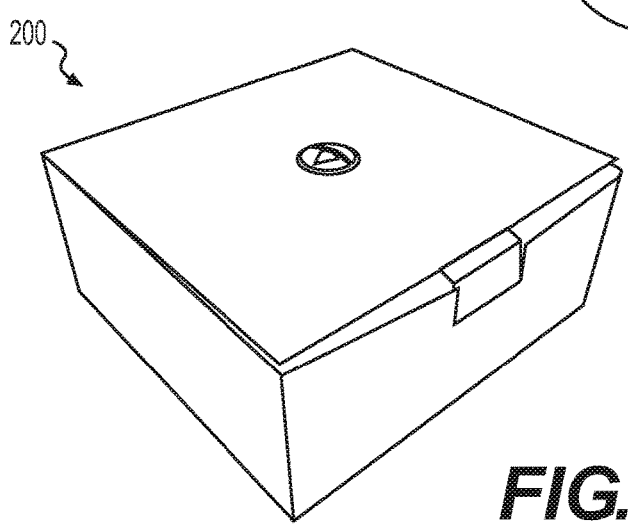
FIG. 22 shows the package for the entire system.

FIG. 22 shows the package 200 for the entire system.

Figure 23:
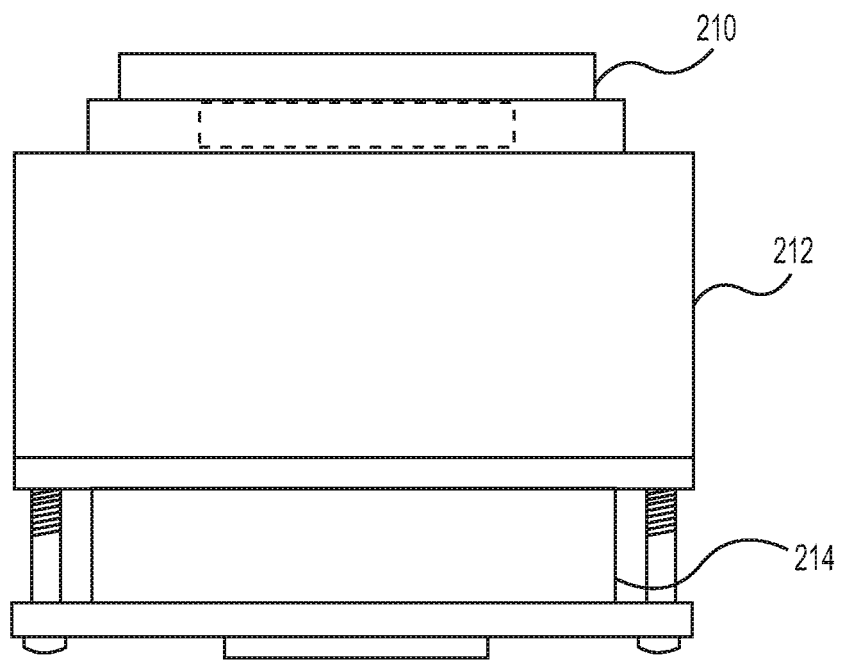
FIG. 23 shows a side view of the pod temperature changer.
Figure 24:
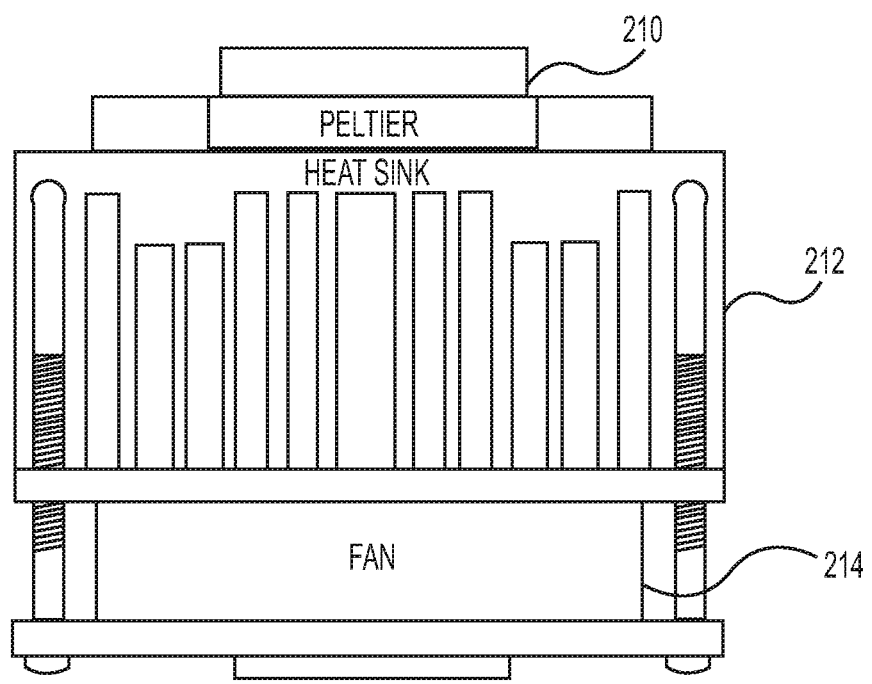
FIG. 24 shows parts of the pod temperature changer.

FIG. 23 shows a side view and FIG. 24 shows a partially cutaway top view of the pod temperature changer 188. In the example of the pod temperature changer 182 is a Peltier cooler 210, the heat sink 212 and the fan 214.

Figures 25, 26:
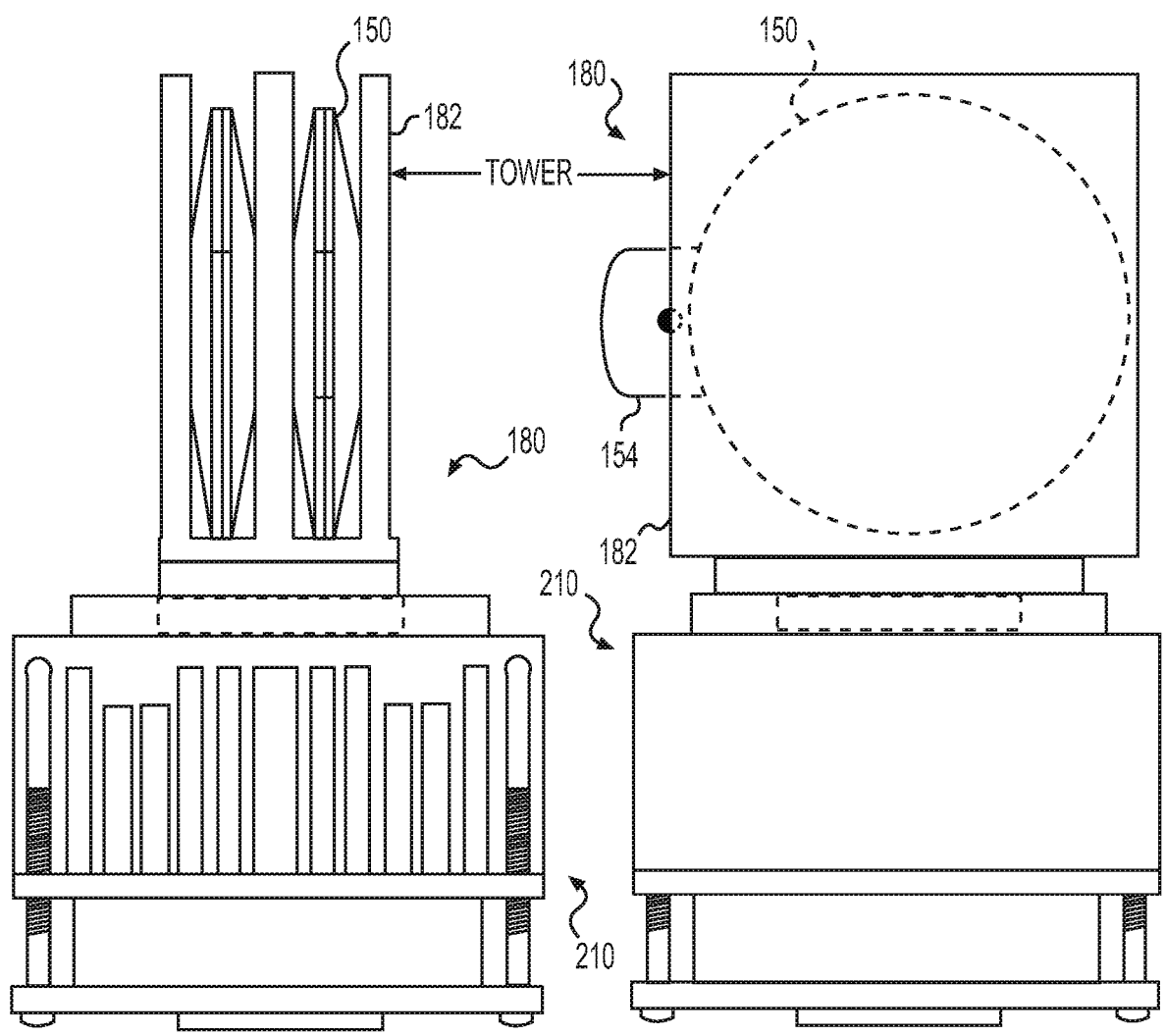
FIG. 25 shows a bottom of the pod temperature changer with the heat transfer fins superimposed.
FIG. 26 shows a side view of the pod temperature changer with a pod between fins.

FIG. 25 shows a partially cutaway top view of the Peltier cooler 210 configured as the pod temperature changer 180 with the three heat transfer fins 182. The superimposed pods 150 are shown between the individual fins. FIG. 26 shows a side view of the pod temperature changer 180 with a pod 150 between fins 182 and a tab 154 extending from the pod.

Figure 27:
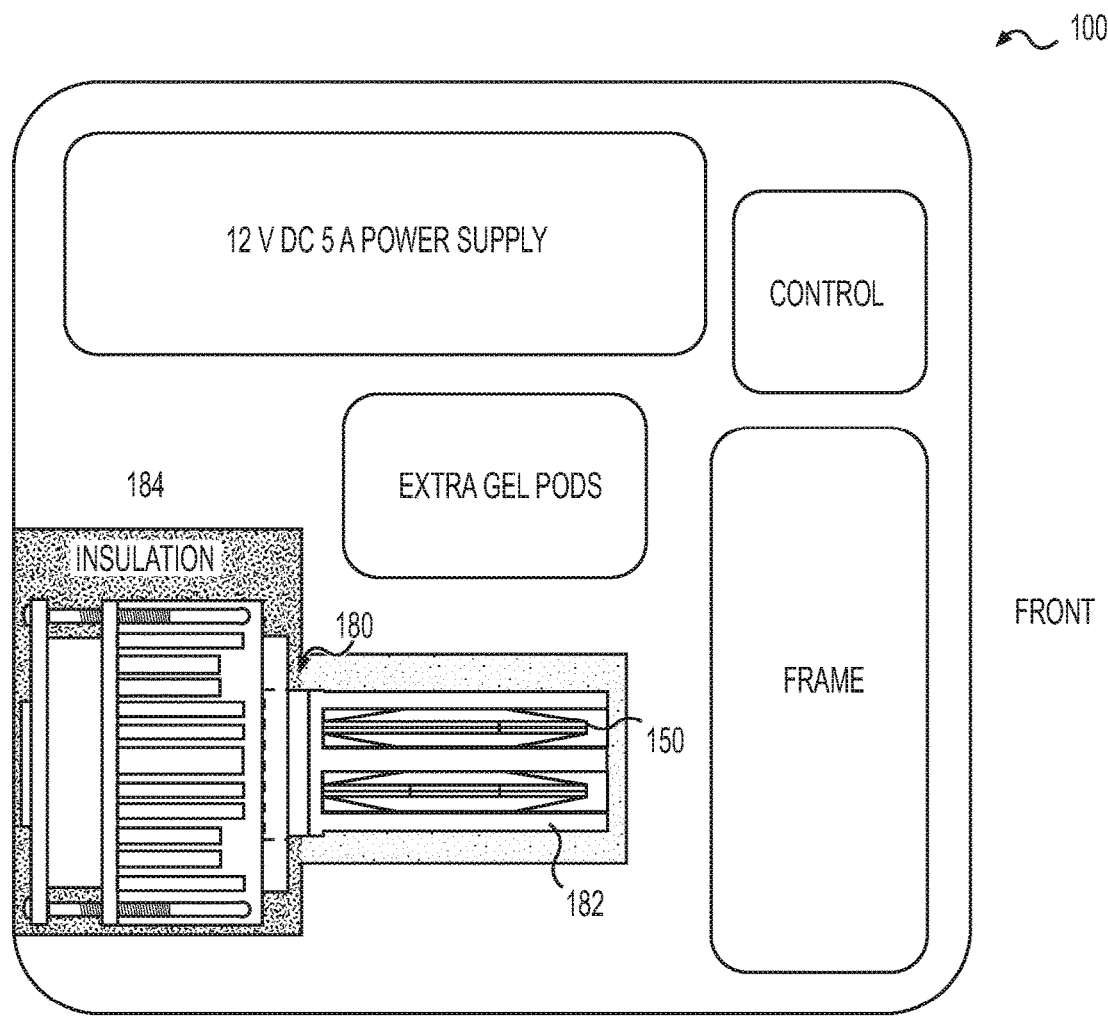
FIG. 27 is a schematic top view of the elements.
Figure 28:
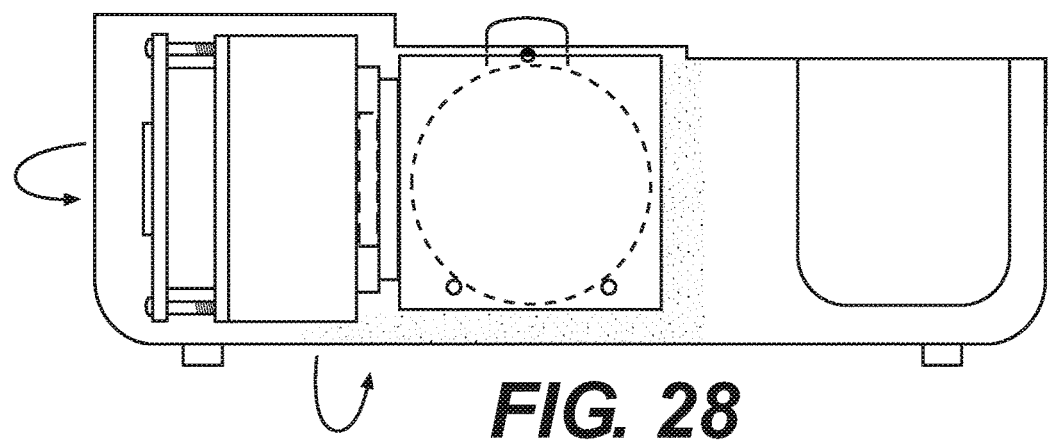
FIG. 28 is a schematic side view of the elements.

FIG. 27 is a schematic top view of the elements in the new system 199. Insulation 184 surrounds the temperature changer 180, in this case a Peltier cold plate cooler with extended fins 182, between which pods 150 are chilled. A 12V DC 5 A power supply and control and an electrical connector are included. Extra gel pods 150 are stored in a second recess and a frame 160 is stored in a third recess. FIG. 28 is a schematic side view of the elements shown in FIG. 26.

The kit includes a carrying case, an inner platform component, a power supply main with cord, a power supply auxiliary plug, a Peltier TE module, a thermal switch, a custom TE exchanger extrusion, insulation for TE extrusion, a DPDT switch, LED indicators, a 12 VDC entrance jack, six pods, goggles, goggle insulation, neodymium magnets, a display box, labels and an instruction sheet.

The Peltier thermo-electric (TE) 12V 5 A cooler module and heat sink assembly 180 is used in one embodiment of the invention. The TE unit connects to 12V 5 A+ power supply and cools an aluminum plate and fins in a short time.

The Peltier Module is 40 mm×40 mm/1.6"×⅙"
The aluminum plate is 40 mm×60 mm/1.6"×2.4"
The heat sink is 90 mm×90 mm/3.5"×3.5?
The whole assembly is approximately 78 mm/3.1" tall
Wire Length: 280 mm/11"
Weight: 455 g
Wattage: 60 W nominal (12V*5 A), 72 W max.

While the invention has been described with reference to specific embodiments, modifications and variations of the invention may be constructed without departing from the scope of the invention, which is defined in the following claims.

We claim:

1. Apparatus comprising a storer and a temperature changer configured for storing and temperature changing treatment of orbital area temperature treatment pods, the storer and the temperature changer having a container base and, an inner partition on the container base the, temperature changer having heat exchange fins and having a heat sink and electrical connections and controls mounted on the container base below the inner partition, the inner partition having recesses in a top of the inner partition, the recesses further comprising at least one temperature changing recess positioned near the heat exchange fins the at least one temperature changing recess being configured for holding at least one orbital area temperature treatment pod adapted for applying to an orbital area of a face, the at least one temperature changing recess being adapted for positioning the at least one temperature treatment pod near the heat exchange fins, the inner partition, further comprising at least one pod storing recess for holding additional pods, the inner partition having a recess for holding an electrical connector and a recess configured for holding a head-mountable frame that is adapted for attaching one or more of the orbital area temperature treatment pods, and positioning the temperature treatment pods against an orbital area of a user's head, at least one orbital heating or cooling pod applied for fitting in the at least one temperature changing recess for applying to an orbital area of a face, the head-mountable a frame for supporting the at least one heating or cooling pod against the orbital area, the at least one pod having at least one tab connected to and extending from the at least one pod and having a fastener on an end of the tab remote from the at least one pod, the head-mountable frame having an attachment for contacting a head of a user and for receiving and holding the at least one tab and holding the at least one pod against the orbital area of the face of the user.

2. The apparatus of claim 1, wherein the frame has a cross member having one or more cross pieces, nose piece connected to a center of the cross member, hinges at opposite ends of the cross member, temples connected to the hinges and one or more receivers on the cross member for receiving and holding the tab.

3. The apparatus of claim 2, wherein the one or more receivers have one or more cooperating fasteners for connecting to the fastener on the tab of the pod.

4. The apparatus of claim 3, wherein the fastener and the one or more cooperating fasteners are magnet and magnet attracting material fasteners.

5. The apparatus of claim 3, further comprising a downward extension from the frame for holding the pod rearward into the orbital area.

6. The apparatus of claim 2, wherein the one or more cross pieces are first and second lenses, wherein the nose piece connects the first and second lenses, wherein the hinges are connected to the first and second lenses remote from the nose piece, and wherein the receivers are connected to tops of the first and second lenses.

7. The apparatus of claim 6, wherein the receivers are upward extensions that have downward opening grooves holding tops of the lenses and having the complementary fasteners for connecting to the fasteners on the tabs that are connected to the one or more pods.

8. The apparatus of claim 1, further comprising a pod storer and temperature changer for holding and changing temperature of the one or more pods.

9. The apparatus of claim 8, wherein the storer and temperature changer is a container with an inner partition with a lower surface covering electrical connections and controls, and a temperature changer having pod temperature changer fins attached to the temperature changer, and having a heat sink.

10. The apparatus of claim 9, wherein the inner partition has an upper surface with first cavities for holding pods adjacent the temperature changer fins.

11. The apparatus of claim 10, wherein the inner partition has a second cavity for holding pods, a third cavity for holding the frame and a fourth cavity for holding an electrical connector.

12. The apparatus of claim 9, wherein the pod temperature changer and electrical connections and controls are mounted on the lower surface of the inner partition.

13. The apparatus of claim 9, further comprising a handle connected to a container, at least one hinge connected to the container and a cover connected to the at least one hinge.

14. The apparatus of claim 1, wherein the electrical connections and controls and the heat exchanger are mounted on the container base and the inner partition, and the recesses are in the top of the inner partition.

15. The apparatus of claim 1, wherein the container has apertures for circulating ambient air to the heat sink.

16. The apparatus of claim 1, wherein the heat exchange fins comprise three parallel heat exchange fins, and wherein the at least one temperature changing recess and the at least one pod storing recess further comprise two parallel recesses.

17. The apparatus of claim 16, wherein the container further comprises a handle and one or more hinges on the container base and a cover connected to the hinges.

18. The apparatus of claim 17, further comprising temperature treatment pods, the electrical connector and the frame in the respective recesses.

19. The apparatus of claim 17, further comprising a carton for enclosing the container, the inner partition, the electrical connection, the temperature changer, the pods, the electrical connector, the frame, the handle and the cover as a complete system ready for use as instructed by a professional.

* * * * *